United States Patent
Ben Hassen et al.

(10) Patent No.: US 11,445,108 B1
(45) Date of Patent: Sep. 13, 2022

(54) TURN DIRECTION GUIDANCE OF AN ENDOSCOPIC DEVICE

(71) Applicant: INTERNATIONAL BUSINESS MACHINES CORPORATION, Armonk, NY (US)

(72) Inventors: Saniya Ben Hassen, Amstelveen (NL); Marc P. Yvon, Antony (FR); Anthony Herve, Paris (FR); Christel Beaujard, Bazainville (FR)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/249,557

(22) Filed: Mar. 5, 2021

(51) Int. Cl.
*H04N 5/232* (2006.01)
*H04N 7/18* (2006.01)
*G06K 9/62* (2022.01)
*G06T 7/70* (2017.01)
*G06T 7/00* (2017.01)
(Continued)

(52) U.S. Cl.
CPC ..... *H04N 5/23222* (2013.01); *A61B 1/00006* (2013.01); *A61B 34/20* (2016.02); *G06K 9/6201* (2013.01); *G06T 7/0012* (2013.01); *G06T 7/60* (2013.01); *G06T 7/70* (2017.01); *H04N 5/23299* (2018.08); *H04N 7/183* (2013.01); *A61B 2034/2065* (2016.02); *G06T 2207/10068* (2013.01); *G06T 2207/30004* (2013.01); *H04N 2005/2255* (2013.01)

(58) Field of Classification Search
CPC ........... H04N 5/23222; H04N 5/23299; H04N 7/183; H04N 2005/2255; A61B 1/00006; A61B 34/20; A61B 2034/2065; G06K 9/6201; G06T 7/0012; G06T 7/60; G06T 7/70; G06T 2207/10068; G06T 2207/30004
See application file for complete search history.

(56) References Cited

U.S. PATENT DOCUMENTS 9,324,145 B1  4/2016  Cherevatsky
9,545,192 B2  1/2017  Braun
(Continued)

FOREIGN PATENT DOCUMENTS

WO  2020016886 A1  1/2020

OTHER PUBLICATIONS

Baguley et al., "Appliance Science: How robotic vacuums navigate", Oct. 6, 2015, cnet, 16 pages.
(Continued)

*Primary Examiner* — James M Pontius
(74) *Attorney, Agent, or Firm* — L. Jeffrey Kelly

(57) ABSTRACT

Method and system are provided for direction guidance of an endoscopic device in a tubular organ. The method receives a current image frame from a camera disposed on the endoscopic device, where the current image frame captures a visible lumen of the tubular organ. The method determines an area of the visible lumen in the current image frame and a ratio of the area of the visible lumen to a minimum enclosing circle of the visible lumen. If the ratio breaches a defined threshold, the method adjusts a target direction of the endoscopic device in a direction from a center of the visible lumen towards a center of the image frame and outputs a notification of the adjusted target direction to a controller of the endoscopic device.

18 Claims, 9 Drawing Sheets

(51) Int. Cl.
  *A61B 34/20* (2016.01)
  *A61B 1/00* (2006.01)
  *G06T 7/60* (2017.01)
  *H04N 5/225* (2006.01)

(56) References Cited

U.S. PATENT DOCUMENTS 10,646,288 B2    5/2020  Yeung
2010/0283841 A1* 11/2010 Tanaka .................... A61B 1/31
                                                    348/E7.085
2020/0113422 A1  4/2020  Wang

OTHER PUBLICATIONS

Bernth et al., "A Novel Robotic Meshworm with Segment-Bending Anchoring for Colonoscopy", IEEE Robotics and Automation Letters, vol. 2, No. 3, Jul. 2017, 8 pages.

Brandon, "Make a Wall Avoiding Robot!", https://www.instructables.com/Make-a-wall-avoiding-Robot!/, instructables circuits. Accessed on Jan. 5, 2021, 27 pages.

Buselli et al., "Evaluation of friction enhancement through soft polymer micro-patterns in active capsule endoscopy", OP Publishing, Measurement Science and Technology, Meas. Sci. Technol. 21 (2010) 105802 (7pp).

Gumprecht et al., "Navigation of a robotic capsule endoscope with a novel ultrasound tracking system", Technical Paper, Published: Jun. 14, 2013, Microsystem Technologies 19, 1415-1423, SpringerLink.

Lee et al., "An elastic caterpillar-based self-propelled robotic colonoscope with high safety and mobility", ScienceDirect, Mechatronics, vol. 39, Nov. 2016, pp. 54-62.

Macek et al., "A control method for stable and smooth path following of mobile robots", Conference Paper, Publication Date: 2005, ETH Zurich, Research Collection, 7 pages.

Prendergast et al., "A Platform for Developing Robotic Navigation Strategies in a Deformable, Dynamic Environment", IEEE Robotics and Automation Letters, vol. 3, No. 3, Jul. 2018, pp. 2670-2677.

Ravankar et al., "Path Smoothing Techniques in Robot Navigation: State-of-the-Art, Current and Future Challenges", sensors, MDPI, Review, Sensors 2018, 18, 3170; doi:10.3390/s18093170, 30 pages.

Robotc, "Wall Detection A Sonic Sojourn", Sensing, © Carnegie Mellon Robotics Academy / For use with Lego® Mindstorms® Education NXT software and base set 9797, pp. 1-9, Jul. 2006.

Tian et al., "A Recursive Otsu-Iris Filter Technique for High-Speed Detection of Lumen Region from Endoscopic images", ©2001 IEEE, pp. 182-186.

Valdastri et al., "Magnetic air capsule robotic system: proof of concept of a novel approach for painless colonoscopy", Surg Endosc (2012) 26:1238-1246.

Wang et al., "An Earthworm-Like Microrobot for Colonoscopy", Instrumentation Research, Biomedical nstrumentation &Technology, Downloaded from http://meridian.allenpress.com/doi/pdf/10.2345/0899-8205-40-6-471.1, Nov./Dec. 2006, pp. 471-478.

Zabulis et al., "Lumen detection for capsule endoscopy", 2008 IEEE/RSJ International Conference on Intelligent Robots and Systems, Acropolis Convention Center, Nice, France, Sep. 22-26, 2008, ©2008 IEEE, pp. 3921-3926.

Mell et al., "The NIST Definition of Cloud Computing", Recommendations of the National Institute of Standards and Technology, Special Publication 800-145, Sep. 2011, 7 pages.

* cited by examiner

TURN DIRECTION GUIDANCE OF AN ENDOSCOPIC DEVICE

BACKGROUND

The present invention relates to a computer implemented method, data processing system and computer program product for endoscopic guidance, and more specifically, to turn direction guidance of an endoscopic device in real-time.

Endoscopies are medical procedures that allow doctors to inspect internal organs of a body. The most common use is to inspect the gastrointestinal tracts of patients; however, endoscopies may also be used to inspect other hollow organs such as the urinary tract, the ears, nose, throat, and heart. During an endoscopy, a doctor generally uses wired endoscopes equipped with video cameras, a light, and, potentially, surgical instruments. The doctor looks at a video on a computer screen to manually insert and guide an endoscope forward and inspect the walls of the hollow organ being inspected while pulling the endoscope out of the body.

In gastrointestinal endoscopies, their purpose is to detect gastrointestinal diseases such as polyps and cancerous cells early enough for successful treatment. The gastrointestinal tract environment is a very specific environment due to its elasticity, the presence of obstacles, the texture and look of its walls, shape changes due to the digestion process and other biological processes.

An endoscopy can be difficult to carry out without incurring pain to a patient or possibly a tear in a patient, either of which can be a deterrent for a patient. Professionals must be highly qualified to perform an endoscopy and few of them have the experience and capability of reducing pain during the procedure. The world population is aging in rich countries and there is a lack of endoscopy specialists in poorer countries. The need for endoscopies increases while a significant amount of education is required to become a good endoscopy specialist.

In summary, endoscopies can save many lives but are complex and expensive procedures with potential pain and harm to a patient.

SUMMARY

According to an aspect of the present invention there is provided a computer-implemented method for turn direction guidance of an endoscopic device in real-time in a tubular organ, comprising: receiving a current image frame from a camera disposed on the endoscopic device, wherein the current image frame captures a visible lumen of the tubular organ; determining an area of the visible lumen in the current image frame; determining a ratio of an area of a minimum enclosing circle of the visible lumen to the area of the visible lumen; if the ratio breaches a defined threshold, adjusting a target direction of the endoscopic device in a direction from a center of the visible lumen towards a center of the image frame; and outputting a notification of the adjusted target direction to a controller of the endoscopic device.

According to a further aspect of the present invention there is provided a system for turn direction guidance of an endoscopic device in a tubular organ, comprising: a processor and a memory configured to provide computer program instructions to the processor to execute the function of the components: an image frame receiving component for receiving a current image frame from a camera disposed on the endoscopic device, wherein the current image frame captures a visible lumen of the tubular organ; a lumen area determining component for determining an area of the visible lumen in the current image frame; a lumen area size determining component for determining a ratio of an area of a minimum enclosing circle of the visible lumen to the area of the visible lumen; a ratio threshold component for determining if the ratio breaches a defined threshold and a target direction component for adjusting the target direction of the endoscopic device from a center of the visible lumen towards a center of the image frame; and an outputting component for outputting a notification of the adjusted target direction to a controller of the endoscopic device.

According to a further aspect of the present invention there is provided a computer program product for turn direction guidance of an endoscopic device in a tubular organ, the computer program product comprising a computer readable storage medium having program instructions embodied therewith, the program instructions executable by a processor to cause the processor to: receive a current image frame from a camera disposed on the endoscopic device, wherein the current image frame captures a visible lumen of the tubular organ; determine an area of the visible lumen in the current image frame; determine a ratio of an area of a minimum enclosing circle of the visible lumen to the area of the visible lumen; if the ratio breaches a defined threshold, adjust a target direction of the endoscopic device from a center of the visible lumen towards a center of the image frame; and output a notification of the adjusted target direction to a controller of the endoscopic device.

The computer readable storage medium may be a non-transitory computer readable storage medium and the computer readable program code may be executable by a processing circuit.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which.

Figure 1A:
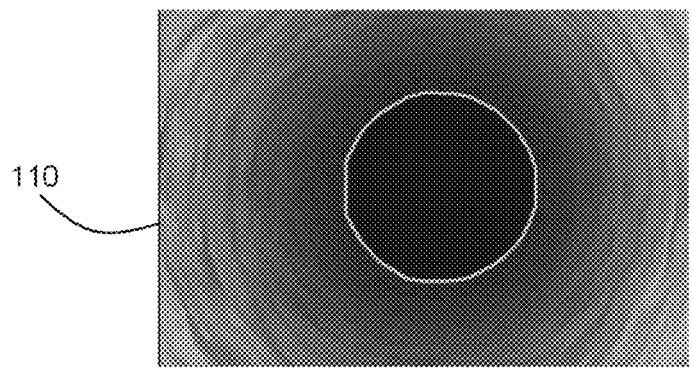
FIGS. 1A to 1C are illustrations of image frames showing lumen areas as used in the described method and system, according to an embodiment.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

As previously described, the present invention relates to a computer implemented method, data processing system and computer program product for endoscopic guidance, and more specifically, to turn direction guidance of an endoscopic device in real-time.

Embodiments of the present invention relate to the field of computing, and more particularly to turn direction guidance of an endoscopic device in real-time. The following described exemplary embodiments provide a system, method, and program product to, among other things, provide an endoscopic guidance system which controls an endoscopic device when inserted into a cavity of a patient. Therefore, the present embodiment has the capacity to improve the technical field of endoscopy by improving guidance of the endoscopic device to decrease contact of the endoscopic device with walls of the cavity of the patient, reducing pain to the patient and damage to the walls of the cavity of the patient.

A method and a system for turn guidance of an endoscopic device in real-time are described. An endoscopic device typically includes a light and a camera for providing images of the inside space of a tubular organ of a patient in which it is being inserted. The endoscopic device may also include a surgical tool for remote manipulation to perform procedures within the tubular organ of the patient. Alternatively, the endoscopic device may be solely for investigative procedures to relay images of the interior of the tubular organ.

The camera provides images of the lumen, which is the inside space of the tubular organ. The lumen is identified as being the darkest area in an image where the light does not reach into the tubular cavity. Methods are known in the art for identifying the lumen area as being the darkest area of an image.

An endoscopic device may be controlled by a human operator, by an automatic controlling system, or a combination of the two. The described guidance system may be used to automatically indicate a target direction for insertion of the endoscopic device into the tubular organ in real-time. The target direction may be used by a human operator or by an automated insertion control system to adjust navigation of the instrument or endoscopic device.

The described target direction guidance interprets frames from the camera to determine if the tubular organ is bending or curving and in which direction it is curving to correct a target direction to avoid a collision by the endoscopic device into a wall of the tubular organ. This is particularly relevant in the context of the proximity of abrupt turns inside an organ like the colon. The method improves the management of the turn phases with the curvature of a tubular organ using the video stream in real-time. The target direction minimizes contact or friction with the wall of the tubular organ thereby reducing pain and internal damage of the patient.

According to the present embodiment, a turn direction guidance program may be a program capable of turn direction guidance of an endoscopic device. The turn direction guidance program may be stored as computer instructions 513 of the computer system 510 of FIG. 5 or stored as an application program 611 of FIG. 6, and is capable of controlling an endoscopic device. A method for a turn direction guidance of an endoscopic device is explained in further detail below.

Figure 1B:
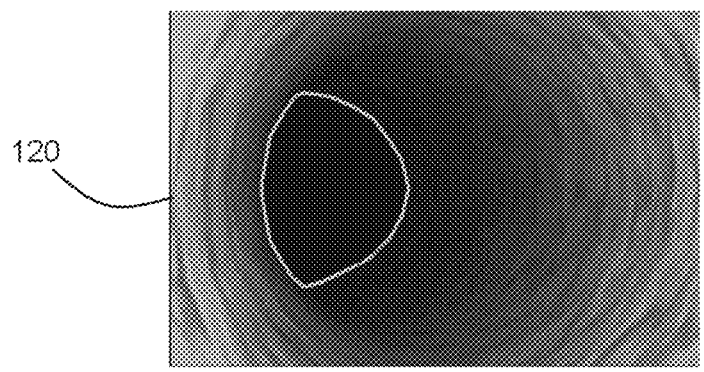
Figure 1C:
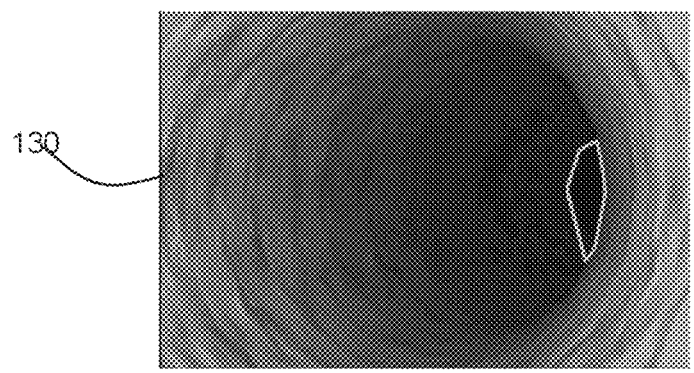

Referring to FIGS. 1A to 1C, three captured image frames 110, 120, 130 are shown to illustrate guidance of an endoscopic device according to the method and associated system described herein. The figures each show an image frame from a camera of an endoscopic device that is inserted in a tubular organ. The light from the endoscopic device illuminates the inside of the tubular organ in which the endoscopic device is inserted and captures the lumen as a dark region that represents the opening of the tubular organ. In FIG. 1A, the tubular organ is not curving and therefore the lumen is shown as a central circular area outlined by a white line for illustration.

In FIG. 1B, the tubular organ is curving to the left and the lumen is therefore decreased in area and is shown to the left in the image. In such a situation, the target direction for insertion of the endoscopic device should be to the right of the lumen area to aim away from a wall of the tubular organ on the left.

In FIG. 1C, an opposite curve is shown with the tubular organ curving to the right in an abrupt manner and the lumen has a decreased area on the right of the image. In such a situation, the target direction should be further to the left of the lumen area to aim away from the wall of the tubular organ on the right.

The fact that the lumen area decreases in the proximity of a curve and the amount of the decrease is used in the described navigation. The position of the lumen in the image is also used to determine a target direction to avoid the inside wall of a curve.

Figure 2A:
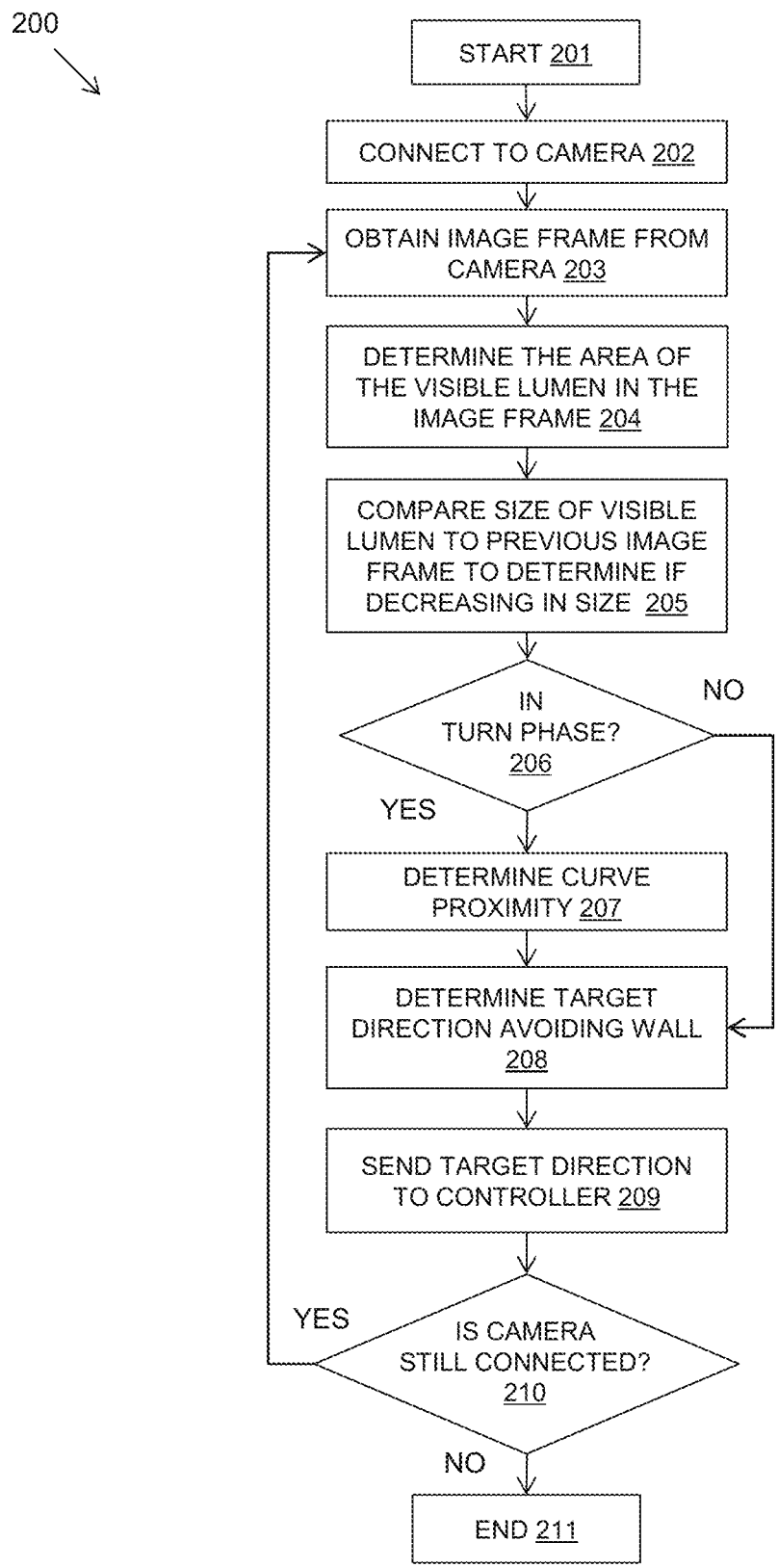
FIG. 2A is a flow diagram of an example embodiment of an aspect of a method in accordance with an embodiment of the present invention.

Referring to FIG. 2A, a flow diagram 200 shows an example embodiment of the described method of direction guidance of an endoscopic device in real-time.

The method may start 201 with a connection established, at block 202, with a camera of the endoscopic device. An image frame is obtained, at block 203, from the camera. The method may work on each image frame in a video stream from the camera or selected image frames in given intervals depending on the frame rate of the video flow sent by the camera and the image processing time.

For the obtained image frame, the method may determine, at block 204, the area of the visible lumen in the image frame. In each image frame, the light from the endoscopic device illuminates the inside of the tubular organ in which the endoscopic device is inserted and captures the lumen as a dark region that represents the opening of the tubular organ. This may be achieved by determining the darkest pixels in terms of color intensity in the image frame. The usual direction for advancing the endoscopic device is the barycenter (also known as the centroid) of the lumen area.

This may be calculated geometrically for the lumen area. However, when the tubular organ includes a turn, a target direction of the barycenter will make the endoscopic device move too close to the inside wall of the curve and, therefore, could induce pain or cause a tear.

The size of the visible lumen in the image frame is compared, at block 205, to the size of the visible lumen in a previous image frame to determine if the size is decreasing. The comparison of the lumen is used to determine, at block 206, if the device is in a turn phrase. If there is an upcoming curve in the tubular organ, the lumen decreases in size over subsequent image frames as the opening of the tract becomes hidden by the curve of the wall of the tubular organ.

A turn phase may be determined, at block 206, by comparing the area of the lumen with the area of the lumen in a preceding frame. If the subsequent lumen area is decreasing, then the device is approaching a turn, whereas if the subsequent area is increasing, the device is moving away from a turn. A notification may be sent to the controller of the endoscopic device to indicate if the motion is moving towards a turn or away from a turn. One method of determining if the area of the lumen is increasing or decreasing is described further in FIG. 2B by comparing a ratio of a minimum enclosing area of the lumen to the lumen area. However, other methods may be used such as a direct comparison of lumen area size between comparable image frames.

If it is determined, at block 206, that the device is not in a turn phase, the target direction is determined, at block 208, as being the barycenter of the lumen. If it is determined, at block 206, that the device is in a turn phase, a proximity of the curve is determined, at block 207, as a trigger for altering the direction to avoid a wall. When the proximity is triggered, a target direction is determined, at block 208, by adjusting the target direction away from the barycenter of the lumen in a given direction for avoiding the inside wall of the turn. This may occur when approaching the turn or when moving away from the turn.

For each image frame, the method sends, at block 209, the target direction to a controller to adjust the target direction to a point where the endoscopic device should set its direction to avoid the inside wall of the curve. The controller may automatically adjust the direction of the endoscopic device or may provide a notification to an operator of the endoscopic device to adjust the direction.

If the camera is still connected, at block 210, the method loops to obtain a next frame from the camera, at block 203, for evaluation of adjustment of the target direction. If the camera is no longer connected, at block 210, the method may end, at block 211.

The method uses the video frames sent by the endoscopic device in real-time, and for each one, determines and sends back the target point on the frame where the endoscope should set its direction. The target point is either the barycenter of the lumen area or an adjusted target a given distance and direction from the barycenter of the lumen. An example embodiment of a method for determining the target distance and direction from the barycenter of the lumen is described with reference to FIG. 2B.

Figure 2B:
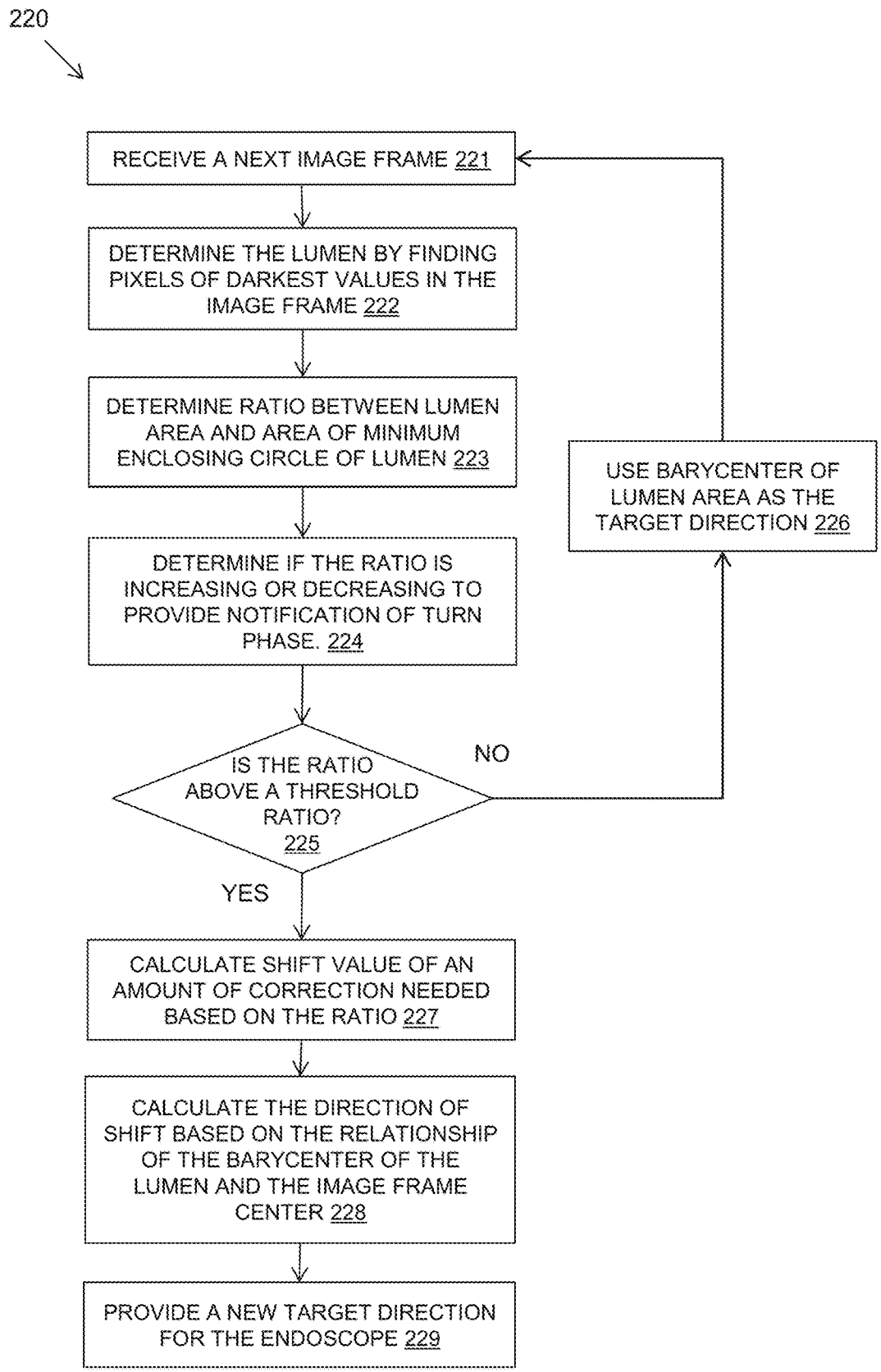
FIG. 2B is a flow diagram of an example embodiment of another aspect of a method in accordance with an embodiment of the present invention.

Referring to FIG. 2B, a flow diagram 220 shows an example embodiment of the described method.

A next image frame is received, at block 221, and the visible lumen area determined, at block 222, by finding the pixels with the darkest values in the image frame and calculating the surface area of the image of the lumen.

The ratio of an area of a minimum enclosing circle of the lumen area to the lumen area (circle area/lumen area) is calculated, at block 223, from the image frame. It may be determined, at block 224, if the ratio is increasing or decreasing compared to the ratio of the preceding image frame (i.e. if the area of the lumen is decreasing or increasing) in order to provide a notification of approaching a turn phase or moving away from the turn to the controller.

It is determined, at block 225, if the ratio breaches a threshold ratio. In the described embodiment, this ratio is breached if it is above a threshold ratio with the ratio being the area of the circle divided by the area of the lumen. The lower the ratio is (i.e. the area of the lumen fills more of the enclosing circle), the further the lumen's barycenter is from the organ wall with a lower risk of wall collision and low risk of pain or damage. The higher the ratio is (i.e. the area of the lumen fills less of the enclosing circle), the closer the lumen's barycenter is to the organ wall and the risk of wall collision due to an abrupt turn is higher with associated higher risk of pain or damage.

The threshold ratio is configured to indicate that the curve is sufficiently close and sharp to require an adjusted direction. If the ratio is not above the threshold ratio, the method uses, at block 226, the barycenter or centroid of the lumen area as the target direction and the method loops to receive, at block 221, a next image frame.

If the ratio is above the threshold ratio, an adjusted target direction is calculated as a shift value of distance and a direction of shift. The method may calculate, at block 227, a shift value of an amount of correction needed, which may be proportionally based on the ratio. A higher ratio requires a greater amount of shift. The method may calculate, at block 228, the direction of shift based on the relationship between the barycenter of the lumen area and the image frame center.

The change in direction takes some time to physically happen. The speed of the endoscopic device's motion is slower than the frame rate of the video. The movement of the endoscopic device must be gentle to avoid abrupt commands. Therefore, from one image to the next, the endoscopic device may point to the center of the image even if the controller instructs it to point to the center of the lumen due to this delay.

The method may provide, at block 229, a new target direction for the endoscopic device in the form of coordinates of a point on the image frame that may be translated into an adjustment to the current direction of the endoscopic device.

The method may be used for guiding wired endoscopes autonomously in real-time within a tract while reducing the risk of pain or tear. A target point may be sent to a controlling robot through their communication interface. The controlling robot may use its motion equipment to move towards that point. This may be repeated for each frame sent by the camera.

Alternatively, the method may be used for guiding an operator of a manually inserted endoscopic device by giving directions, for example, via an interface with a video display of the captured images with the interface indicating the required adjustments to the direction.

Figure 3A:
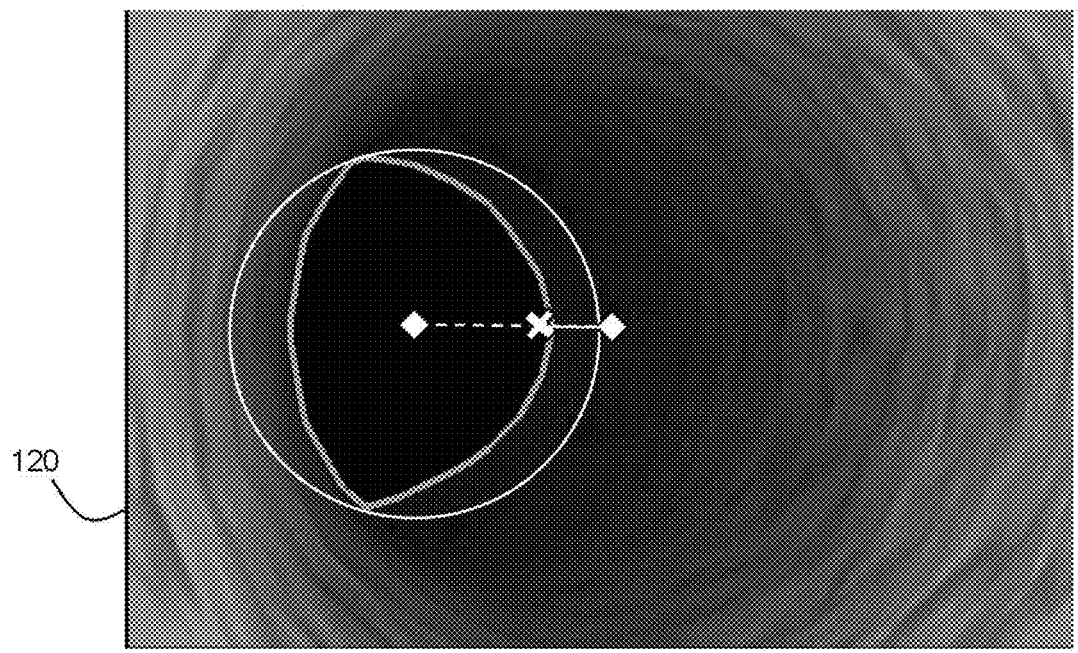
FIGS. 3A and 3B are illustrations of image frames showing example shift distances and directions in accordance with an embodiment of aspects of the present invention.
Figure 3B:
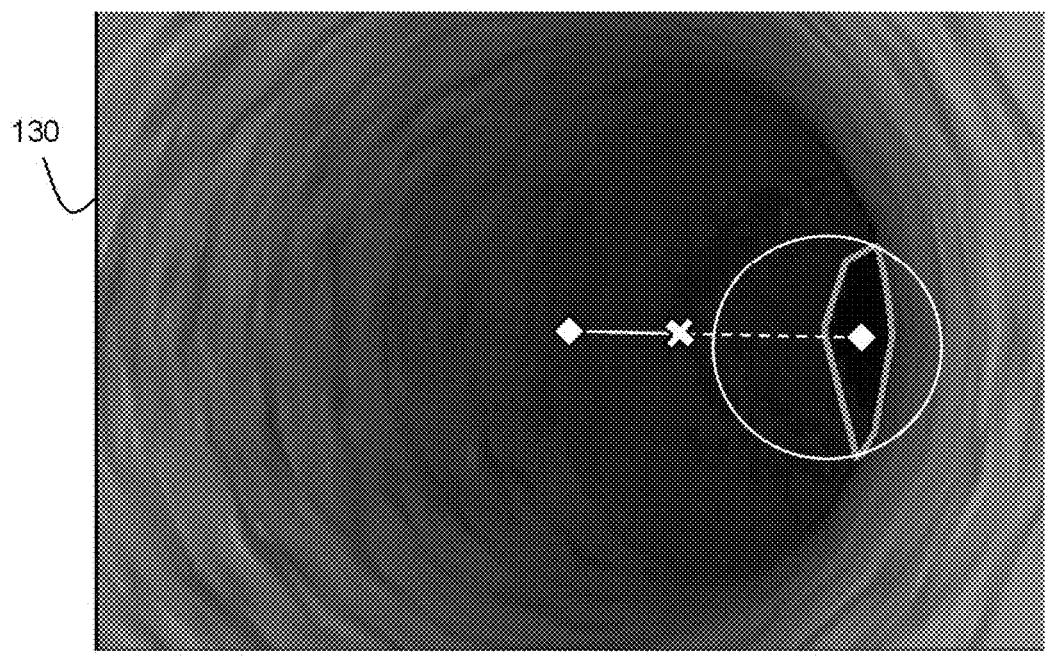

Referring to FIGS. 3A and 3B, an example embodiment of the above method for determining an adjusted target direction by calculating a shift value and a direction of shift is illustrated using the image frames 120, 130 of FIGS. 1B and 1C.

In each of the image frames, the coordinates of the barycenter of the visible lumen area in the image frame is determined as shown by the diamond point in the outlined lumen. The coordinates of the center of the image are also determined as shown by the diamond point in the center of the image outside the lumen. The distance D between the coordinates of the barycenter of the lumen and the coordinates of the center of the image is calculated.

The ratio of the area of a minimum enclosing circle (as shown) to the area of the lumen is calculated. The minimum enclosing circle is a smallest circle which enclosed the lumen. A shifting value is calculated as S={D/ratio} and a direction of the shift is determined as the direction of the lumen barycenter from the image center.

This results in a translation to a target point (shown as a cross in the image frames 120, 130) to apply to the lumen coordinate, said target point is a point at S distance from the center of the image in the direction of the lumen barycenter. As S<D then the position returned is shifting away from the wall. New coordinates of the target point can be obtained from the translation to avoid the wall.

Figure 4A:
FIGS. 4A to 4C are a series of image frames with associated schematic diagrams illustrating a method in accordance with an embodiment of the present invention.
Figure 4A:
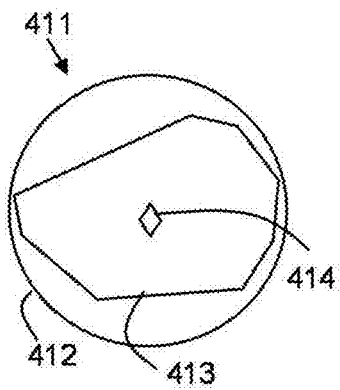
Figure 4B:
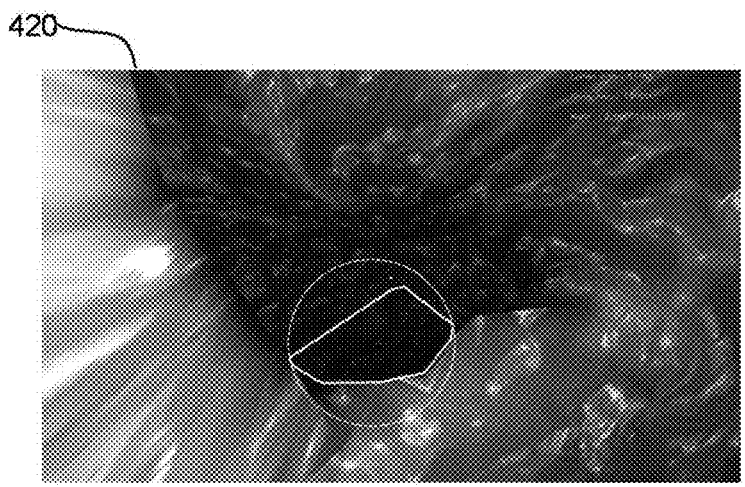
Figure 4B:
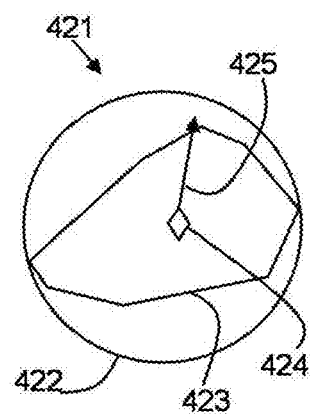
Figure 4C:
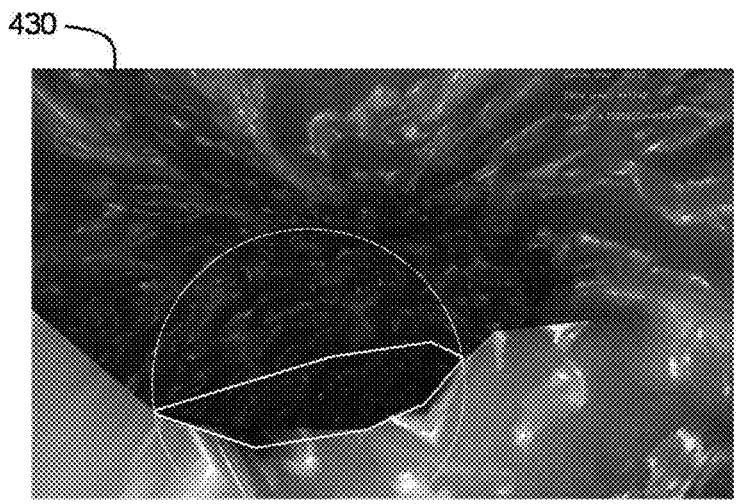
Figure 4C:
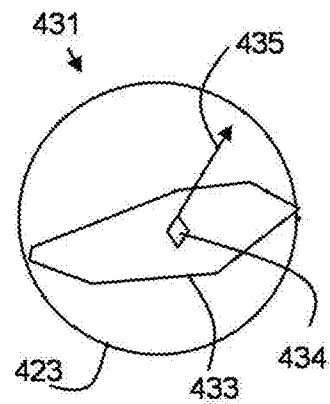

Referring to FIGS. 4A to 4C, a series of three image frames 410, 420, 430 are shown with lumens of decreasing ratio with respect to their minimum enclosing circles.

Referring to FIGS. 4A to 4C, a series of three image frames 410, 420, 430 are shown with increasing ratios of areas of lumen enclosing circles to area of lumens. Each figure shows a diagram 411, 421, 431 of the lumen 413, 423, 433 and enclosing circle 412, 422, 432 with the center of the lumen 414, 424, 434 and the adjusted target direction 425, 435 in FIGS. 4B and 4C. These image frames 410, 420, 430 are used in the example below.

The following phases may be encountered.

Phase 1: Determine approaching turn phase.

If, as the endoscopic device moves forward, the area of the lumen decreases—a turn phase is detected and it may be necessary to avoid a wall during the turn.

If, as the endoscopic device moves forward, the area of the lumen increases—a move away phase is detected and there is no risk.

Phase 2—Determining a curve proximity.

In the turn phase, as the endoscopic device moves forward, the area of the lumen reduces and a ratio is calculated of the area of the minimum lumen enclosing circle to the area of the lumen. The ratio is used as an indication of curve proximity.

In this example, a triggered_ratio is set to 2 (half of the shape is missing) and if (Ratio>Triggered_ratio) then a curve is identified=>turn proximity triggered.

For example:
Image Frame 1 (FIG. 4A):
Area of min-enclosing circle: 106214;
Lumen area: 64037 pixels;
Ratio=1.66=>no turn proximity.
Image Frame 2 (FIG. 4B):
Area of min-enclosing circle: 131051;
Lumen area: 57763 pixels;
Ratio=2.27=>turn proximity.
Image Frame 3 (FIG. 4C):
Area of min-enclosing circle: 441742;
Lumen area: 99210 pixels;
Ratio=4.45=>turn proximity.

Phase 3—Determining direction for avoiding wall.

If (surface circle)/(surface lumen)<Ratio, then Direction=Lumen Barycenter. Else Shift=distance (image_center, lumen_barycenter)/Ratio. In this example, the Ratio-Threshold is set to 2.
Image Frame 1 (FIG. 4A):
Ratio=1.66 Ratio<Ratio-Threshold
direction=D=>lumen barycenter (414)
Image Frame 2 (FIG. 4B):
Ratio=2.27 Ratio>Ratio-Threshold=
=>Shift=D/Ratio (arrow 425)
Image Frame 3 (FIG. 4C):
Ratio=4.45 Ratio>Ratio-Threshold
=>Shift=D/Ratio (arrow 435)

Notifications may be provided to a controller of the endoscopic device as follows:

Sending an alert notification when an imminent turn is detected. This may be based on the decrease in the lumen area between adjacent image frames. If the lumen area is increasing there is no risk as this is a moving away phase.

Sending a proximity notification of a turn. This may be based on the ratio of the minimum enclosing circle area to the lumen area.

Sending a new direction to move away from the wall. This may be based on the determined shift value and direction.

Figure 5:
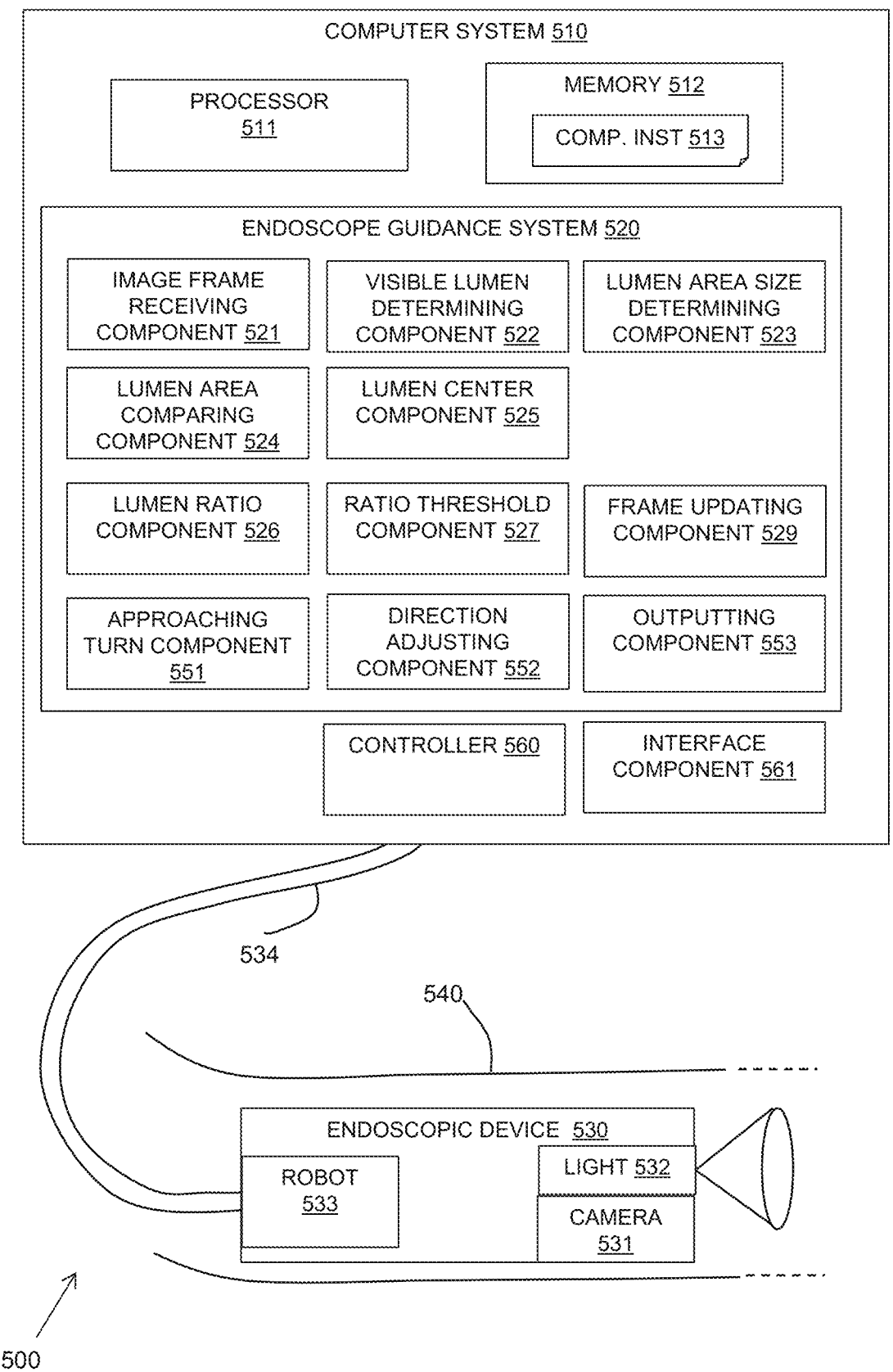
FIG. 5 is block diagram of an example embodiment of a system in accordance with an embodiment of the present invention.

Referring to FIG. 5, a block diagram shows an example embodiment of a system 500. The system 500 includes a computer system 510 connected via a wire 534 to an endoscopic device 530. The endoscopic device 530 is provided having a camera 531, light 532, and a robot 533 for directing the endoscopic device 530 in a tubular organ 540.

The computer system 510 includes at least one processor 511, a hardware module, or a circuit for executing the functions of the described components which may be software units executing on the at least one processor. Multiple processors running parallel processing threads may be provided enabling parallel processing of some or all of the functions of the components. The computer system includes memory 512, which may be configured to provide computer instructions 513 to the at least one processor 511 to carry out the functionality of the components.

An endoscopic guidance system 520 of the computer system 510 provides the described functionality for direction guidance of the endoscopic device 530 in real time.

The endoscopic guidance system 520 includes an image frame receiving component 521 for receiving a current image frame from the camera 531 disposed on the endoscopic device 530 and a frame updating component 529 for analyzing and comparing each image frame received from the camera 531.

The endoscopic guidance system 520 may include: a visible lumen determining component 522 for determining the visible lumen by identifying the darkest pixels in the image frame; a lumen center component 525 for determining a center of the visible lumen as a barycenter of the area of the visible lumen; a lumen area size determining component 523 for determining a size of an area of the visible lumen in the current image frame; and a lumen area comparing component 524 for comparing the size of the area of the visible lumen in the current image frame with a size of an area of visible lumen in a previous image frame.

The endoscopic guidance system 520 may also include: a lumen ratio component 526 for determining a ratio of an area of a minimum enclosing circle of the visible lumen to an area of the visible lumen; a ratio threshold component 527 for determining if the ratio breaches a defined threshold.

The endoscopic guidance system 520 may include an approaching turn component 551 for determining if there is a decrease in the size of the area of the visible lumen indicating an approaching turn in the tubular organ and a direction adjusting component 552 for adjusting the target direction when an approaching turn is output. The direction adjusting component 522 may adjust a target direction of the endoscopic device from an existing direction of a center of the visible lumen towards a center of the image frame. The direction adjusting component 522 may adjust the target direction by a distance proportional to the ratio from an existing direction of a center of the visible lumen towards a center of the image frame.

The endoscopic guidance system 520 may include an outputting component 553 for outputting notifications of whether: the endoscopic device is in a turning phase; is approaching a turn; or a required adjustment to a target direction. The notifications may be output to a controller 560 of the endoscopic device 530. The controller 560 of the endoscopic device 530 may be an automated controller that automatically adjusts a target direction of the endoscopic device. The outputting component 553 may send notifications to an interface component 561 for providing visual notifications and target directions for a human controller.

Figure 6:
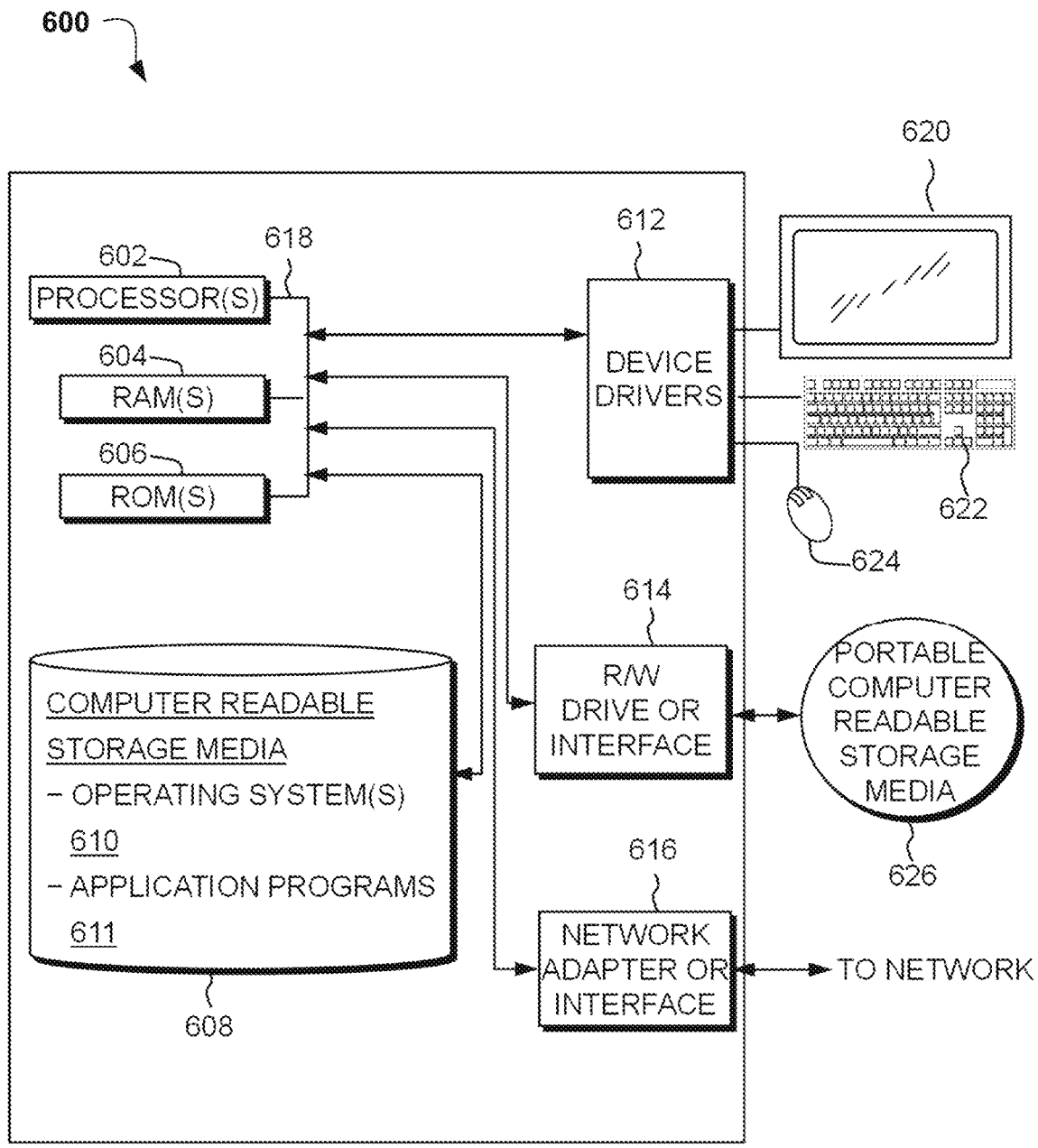
FIG. 6 is a block diagram of an embodiment of a computer system in which the present invention may be implemented, according to an embodiment.

FIG. 6 depicts a block diagram of components of a computing system 600 as used for the computer system 510 of FIG. 5, in accordance with an embodiment of the present invention. It should be appreciated that FIG. 6 provides only an illustration of one implementation and does not imply any limitations with regard to the environments in which different embodiments may be implemented. Many modifications to the depicted environment may be made. Additionally, the computing system 600 may be one of the cloud computing nodes 710 as illustrated and described below with respect to FIG. 7.

The computing system can include one or more processors 602, one or more computer-readable RAMs 604, one or more computer-readable ROMs 606, one or more computer readable storage media 608, device drivers 612, read/write drive or interface 614, and network adapter or interface 616, all interconnected over a communications fabric 618. Communications fabric 618 can be implemented with any architecture designed for passing data and/or control information between processors (such as microprocessors, communications and network processors, etc.), system memory, peripheral devices, and any other hardware components within the system.

One or more operating systems 610, and application programs 611, such as the endoscopic guidance system are stored on one or more of the computer readable storage media 608 for execution by one or more of the processors 602 via one or more of the respective RAMs 604 (which typically include cache memory). In the illustrated embodiment, each of the computer readable storage media 608 can be a magnetic disk storage device of an internal hard drive, CD-ROM, DVD, memory stick, magnetic tape, magnetic disk, optical disk, a semiconductor storage device such as RAM, ROM, EPROM, flash memory, or any other computer readable storage media that can store a computer program and digital information, in accordance with embodiments of the invention.

The computing system can also include a R/W drive or interface 614 to read from and write to one or more portable computer readable storage media 626. Application programs 611 on the computing system can be stored on one or more of the portable computer readable storage media 626, read via the respective RAY drive or interface 614 and loaded into the respective computer readable storage media 608.

The computing system can also include a network adapter or interface 616, such as a TCP/IP adapter card or wireless communication adapter. Application programs 611 on the computing system can be downloaded to the computing device from an external computer or external storage device via a network (for example, the Internet, a local area network or other wide area networks or wireless networks) and network adapter or interface 616. From the network adapter or interface 616, the programs may be loaded into the computer readable storage media 608. The network may comprise copper wires, optical fibers, wireless transmission, routers, firewalls, switches, gateway computers and edge servers.

The computing system can also include a display screen 620, a keyboard or keypad 622, and a computer mouse or touchpad 624. Device drivers 612 interface to display screen 620 for imaging, to keyboard or keypad 622, to computer mouse or touchpad 624, and/or to display screen 620 for pressure sensing of alphanumeric character entry and user selections. The device drivers 612, R/W drive or interface 614, and network adapter or interface 616 can comprise hardware and software stored in computer readable storage media 608 and/or ROM 606.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access a normalized search engine or related data available in the cloud. For example, the normalized search engine could execute on a computing system in the cloud and execute normalized searches. In such a case, the normalized search engine could normalize a corpus of information and store an index of the normalizations at a storage location in the cloud. Doing so allows a user to access this information from any computing system attached to a network connected to the cloud (e.g., the Internet).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
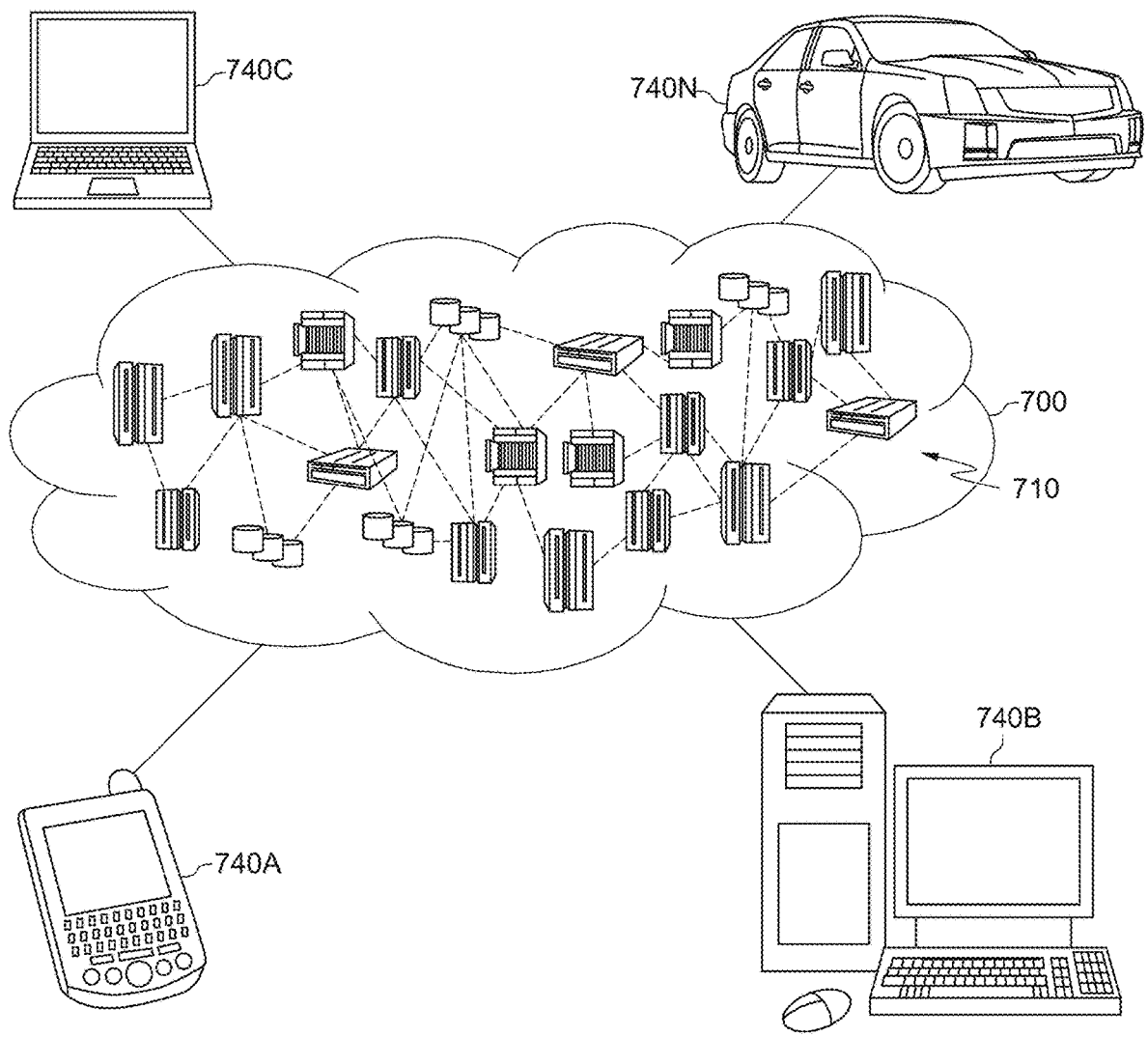
FIG. 7 depicts a cloud computing environment according to an embodiment of the present invention.

Referring now to FIG. 7, illustrative cloud computing environment 700 is depicted. As shown, cloud computing environment 700 includes one or more cloud computing nodes 710 with which local computing devices used by cloud consumers, such as, for example, personal digital assistant (PDA) or cellular telephone 740A, desktop computer 740B, laptop computer 740C, and/or automobile computer system 740N may communicate. Cloud computing nodes 710 may communicate with one another. They may be grouped (not shown) physically or virtually, in one or more networks, such as Private, Community, Public, or Hybrid clouds as described hereinabove, or a combination thereof. This allows cloud computing environment 700 to offer infrastructure, platforms and/or software as services for which a cloud consumer does not need to maintain resources on a local computing device. It is understood that the types of computing devices 740A-N shown in FIG. 7 are intended to be illustrative only and that cloud computing nodes 710 and cloud computing environment 700 can communicate with any type of computerized device over any type of network and/or network addressable connection (e.g., using a web browser).

Figure 8:
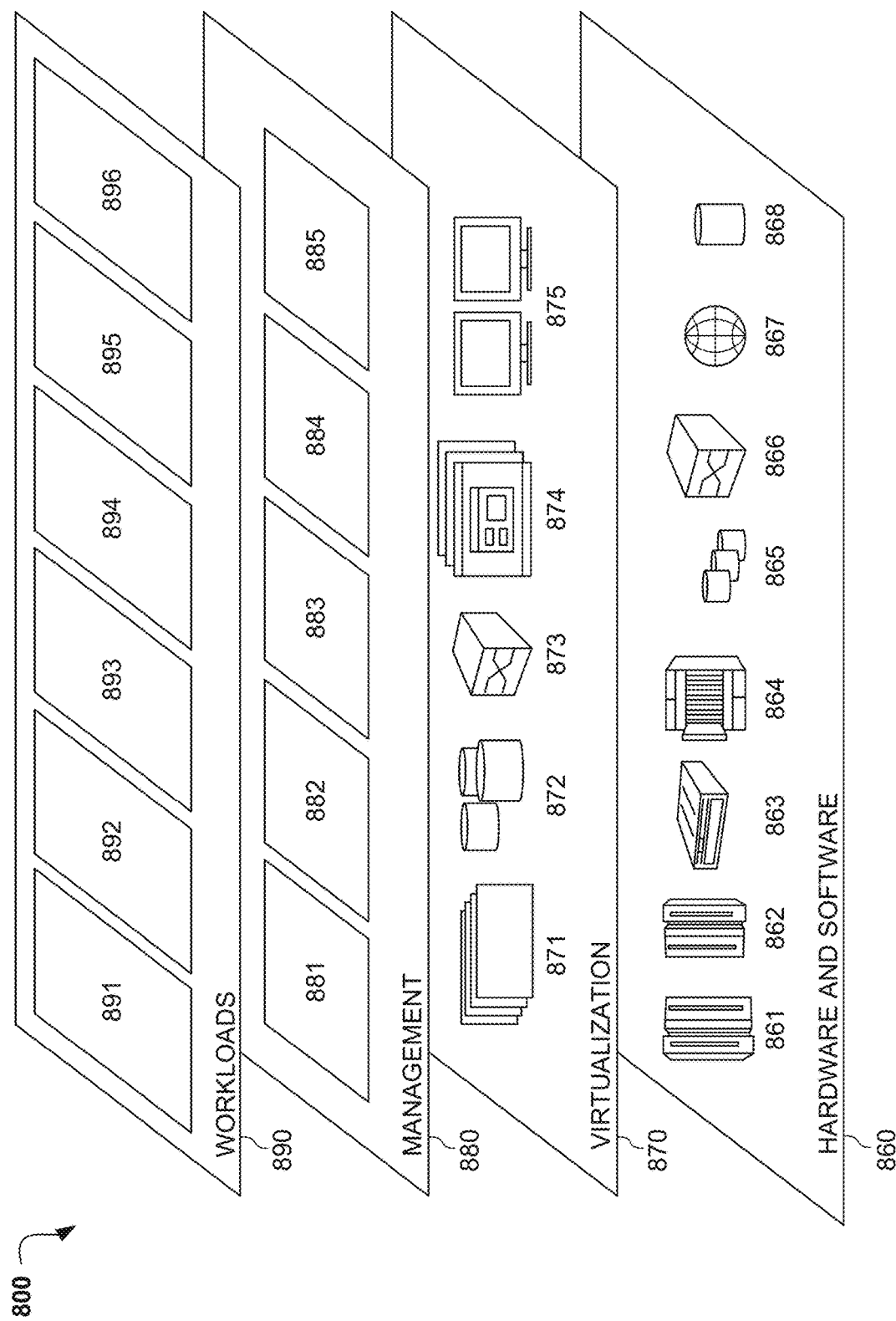
FIG. 8 depicts abstraction model layers according to an embodiment of the present invention.

Referring now to FIG. 8, a set of functional abstraction layers 800 provided by cloud computing environment 700 (as shown in FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872, for example the computer readable storage media 608 as shown in FIG. 6; virtual networks 873, including virtual private networks; virtual applications and operating systems 874; and virtual clients 875.

In an example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In an example, these resources may include application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and endoscopy control 896. The endoscopy control 896 may provide control of an endoscopy device during an endoscopy exam by a doctor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for turn direction guidance of an endoscopic device in real-time in a tubular organ, comprising:
   receiving a current image frame from a camera disposed on the endoscopic device, wherein the current image frame captures a visible lumen of the tubular organ;
   determining an area of the visible lumen in the current image frame;
   determining a ratio of an area of a minimum enclosing circle of the visible lumen to the area of the visible lumen;
   upon determining the ratio breaches a defined threshold, adjusting a target direction of the endoscopic device in a direction from a center of the visible lumen towards a center of the current image frame;
   outputting a notification of the adjusted target direction to a controller of the endoscopic device;
   comparing the ratio of the current image frame with a ratio of a previous image frame;
   determining there is a decrease in a size of the area of the visible lumen indicating an approaching turn in the tubular organ; and
   upon determining there is a decrease in the size of the area of the visible lumen, outputting a notification of the approaching turn to the controller of the endoscopic device.

2. The computer-implemented method according to claim 1, wherein
   upon determining the ratio breaches the defined threshold, adjusting the target direction by a distance proportional to the ratio from an existing direction towards the center of the image frame.

3. The computer-implemented method according to claim 2, wherein
   the distance is a measurement between the center of the visible lumen and the center of the image frame.

4. The computer-implemented method according to claim 1, wherein
   the determining the the ratio breaches the defined threshold is determined when the visible lumen is a configured amount less than the area of the minimum enclosing circle, indicating that turn is in progress.

5. The computer-implemented method according to claim 1, wherein
   the controller of the endoscopic device is an automated controller that automatically adjusts the target direction of the endoscopic device.

6. The computer-implemented method according to claim 1, further comprising:
   outputting a notification of the adjusted target direction to the controller of the endoscopic device; and
   providing a visual indication of a target direction on a user interface.

7. The computer-implemented method according to claim 1, further comprising:
   including iterating the method for each of a selection of image frames received from the camera and outputting notifications in real-time.

8. The computer-implemented method according to claim 1, wherein
   the visible lumen is determined by identifying the darkest pixels in the image frame, and
   a center of the visible lumen is calculated as a barycenter of the area of the visible lumen.

9. A computer program product for turn direction guidance of an endoscopic device in a tubular organ, the computer program product comprising:
   one or more computer-readable tangible storage medium and program instructions stored on at least one of the one or more tangible storage medium, the program instructions executable by a processor, the program instructions the program instructions readable by a computing system to cause the computing system to perform a method comprising:
   receiving a current image frame from a camera disposed on the endoscopic device, wherein the current image frame captures a visible lumen of the tubular organ;
   determining an area of the visible lumen in the current image frame;
   determining a ratio of a minimum enclosing circle of the visible lumen to the area of the visible lumen;
   upon determining the ratio breaches a defined threshold, adjusting a target direction of the endoscopic device from a center of the visible lumen towards a center of the current image frame;
   outputting a notification of the adjusted target direction to a controller of the endoscopic device;
   comparing the ratio of the current image frame with a ratio of a previous image frame;
   determining there is a decrease in a size of the area of the visible lumen indicating an approaching turn in the tubular organ;

upon determining there is a decrease in the size of the area of the visible lumen, outputting a notification of the approaching turn to the controller of the endoscopic device.

10. A computer system for turn direction guidance of an endoscopic device in real-time in a tubular organ, the computer system comprising:
   one or more computer processors, one or more computer-readable storage media, and program instructions stored on the one or more of the computer-readable storage media for execution by at least one of the one or more processors, wherein the computer system is capable of performing a method comprising:
   receiving a current image frame from a camera disposed on the endoscopic device, wherein the current image frame captures a visible lumen of the tubular organ;
   determining an area of the visible lumen in the current image frame;
   determining a ratio of an area of a minimum enclosing circle of the visible lumen to the area of the visible lumen;
   upon determining the ratio breaches a defined threshold, adjusting a target direction of the endoscopic device in a direction from a center of the visible lumen towards a center of the current image frame;
   outputting a notification of the adjusted target direction to a controller of the endoscopic device comparing the ratio of the current image frame with a ratio of a previous image frame;
   determining there is a decrease in a size of the area of the visible lumen indicating an approaching turn in the tubular organ; and
   upon determining there is a decrease in the size of the area of the visible lumen, outputting a notification of the approaching turn to the controller of the endoscopic device.

11. The computer system according to claim 10, wherein upon determining the ratio breaches the defined threshold, adjusting the target direction by a distance proportional to the ratio from an existing direction towards the center of the image frame.

12. The computer system according to claim 11, wherein the distance is a measurement between the center of the visible lumen and the center of the image frame.

13. The computer system according to claim 10, wherein the determining the ratio breaches the defined ratio is determined when the visible lumen is a configured amount less than the area of the minimum enclosing circle, indicating that turn is in progress.

14. The computer system according to claim 10, wherein the controller of the endoscopic device is an automated controller that automatically adjusts the target direction of the endoscopic device.

15. The computer system according to claim 10, further comprising:
   outputting a notification of the adjusted target direction to the controller of the endoscopic device; and
   providing a visual indication of a target direction on a user interface.

16. The computer system according to claim 10, further comprising:
   including iterating the method for each of a selection of image frames received from the camera and outputting notifications in real-time.

17. The computer system according to claim 10, wherein the visible lumen is determined by identifying the darkest pixels in the image frame, and
   a center of the visible lumen is calculated as a barycenter of the area of the visible lumen.

18. A computer-implemented method for turn direction guidance of an endoscopic device in real-time in a tubular organ, comprising:
   receiving a current image frame from a camera disposed on the endoscopic device, wherein the current image frame captures a visible lumen of the tubular organ;
   determining an area of the visible lumen in the current image frame;
   determining a ratio of an area of a minimum enclosing circle of the visible lumen to the area of the visible lumen;
   upon determining the ratio breaches a defined threshold, adjusting a target direction of the endoscopic device in a direction from a center of the visible lumen towards a center of the current image frame;
   outputting a notification of the adjusted target direction to a controller of the endoscopic device;
   comparing the ratio of the current image frame with a ratio of a previous image frame;
   determining there is an increase in a size of the area of the visible lumen indicating a moving away from a turn in the tubular organ; and
   upon determining there is an increase in the size of the area of the visible lumen, outputting a notification of a the moving away from the turn to the controller of the endoscopic device.

* * * * *